(12) United States Patent
Hynna et al.

(10) Patent No.: US 9,914,211 B2
(45) Date of Patent: Mar. 13, 2018

(54) HAND-GUIDED AUTOMATED POSITIONING DEVICE CONTROLLER

(71) Applicant: Synaptive Medical (Barbados) Inc., Bridgetown (BB)

(72) Inventors: Kai Hynna, Toronto (CA); Kelly Dyer, Toronto (CA); Cameron Piron, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 14/898,928

(22) PCT Filed: Nov. 25, 2014

(86) PCT No.: PCT/CA2014/051123
§ 371 (c)(1),
(2) Date: Dec. 16, 2015

(87) PCT Pub. No.: WO2016/082019
PCT Pub. Date: Jun. 2, 2016

(65) Prior Publication Data
US 2017/0252921 A1    Sep. 7, 2017

(51) Int. Cl.
| | |
|---|---|
| *B25J 9/16* | (2006.01) |
| *B25J 13/00* | (2006.01) |
| *A61B 34/20* | (2016.01) |
| *A61B 34/32* | (2016.01) |
| *A61B 17/00* | (2006.01) |

(Continued)

(52) U.S. Cl.
CPC ......... *B25J 9/161* (2013.01); *A61B 17/00234* (2013.01); *A61B 34/20* (2016.02); *A61B 34/32* (2016.02); *A61B 34/74* (2016.02); *A61B 42/10* (2016.02); *A61B 90/98* (2016.02); *B25J 13/006* (2013.01); *A61B 2017/00207* (2013.01);

(Continued)

(58) Field of Classification Search
CPC .......... B25J 9/161; A61B 34/20; A61B 34/32; A61B 34/74; A61B 42/10; A61B 90/98
See application file for complete search history.

(56) References Cited

U.S. PATENT DOCUMENTS 8,054,184 B2 *  11/2011  Cline ................. A61B 1/00059
                                                                340/10.1
9,533,412 B2 *   1/2017  Ishige .................... B25J 9/0096

(Continued)

FOREIGN PATENT DOCUMENTS

EP    1768747 A2    4/2007
EP    2594197 A1    5/2013

(Continued)

*Primary Examiner* — Ian Jen
(74) *Attorney, Agent, or Firm* — Ridout & Maybee LLP

(57) ABSTRACT

An automated positioning device and associated method for use in a medical procedure is provided. The automated positioning device comprises a computing device having a processor coupled to a memory, a multi-joint positioning arm electrically coupled to the computing device and controlled by the computing device, and a sensor module attached to the multi-joint positioning arm and providing a proximity signal to the computing device indicating proximity of a target. The computing device provides a control signal to the multi-joint positioning arm to move the multi-joint positioning arm in response to the proximity signal.

12 Claims, 9 Drawing Sheets

(51) Int. Cl.
    *A61B 34/00*     (2016.01)
    *A61B 42/10*     (2016.01)
    *A61B 90/98*     (2016.01)
    *A61B 90/00*     (2016.01)

(52) U.S. Cl.
    CPC .............. *A61B 2017/00973* (2013.01); *A61B 2034/2057* (2016.02); *A61B 2090/3983* (2016.02)

(56) References Cited

U.S. PATENT DOCUMENTS

| | | | |
|---|---|---|---|
| 9,668,768 B2* | 6/2017 | Piron ................ | A61B 17/3421 |
| 2005/0154295 A1 | 7/2005 | Quistgaard et al. | |
| 2005/0273199 A1* | 12/2005 | Ban ...................... | B25J 9/1682 |
| | | | 700/248 |
| 2006/0142656 A1* | 6/2006 | Malackowski .... | A61B 17/1626 |
| | | | 600/424 |
| 2008/0009965 A1 | 1/2008 | Bruemmer et al. | |
| 2012/0259178 A1 | 10/2012 | Kim et al. | |
| 2012/0265071 A1* | 10/2012 | Berke ................ | A61B 1/00149 |
| | | | 600/439 |
| 2014/0330114 A1* | 11/2014 | Navab .................. | A61B 1/041 |
| | | | 600/424 |

FOREIGN PATENT DOCUMENTS

| | | | |
|---|---|---|---|
| EP | 2647475 A2 | 10/2013 | |
| WO | WO 2011/060185 A1 | 5/2011 | |

\* cited by examiner

HAND-GUIDED AUTOMATED POSITIONING DEVICE CONTROLLER

TECHNICAL FIELD

The present disclosure is generally related to image guided medical procedures, and more specifically to a sensor based hand guided automated positioning device controller.

BACKGROUND

The present disclosure is generally related to image guided medical procedures using a surgical instrument, such as a fiber optic scope, an optical coherence tomography (OCT) probe, a micro ultrasound transducer, an electronic sensor or stimulator, or an access port based surgery, where a medical navigation system includes a robotic arm for assisting a surgeon.

Optical tracking systems used in the medical procedure track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Conventional systems have infrared (IR) cameras that track reflective markers such as balls placed on a frame on a pointer, port, or positioning device arm. Additionally, a robotic arm may automatically position and focus a camera on a surgical site of interest based on position information received from the optical tracking camera images.

Such robotic arm positioning systems occasionally interfere with the surgeon, requiring the surgeon to manually move the robotic arm to a different position. Conventional robotic arms can be awkward at times to manually position. Conventionally, the surgeon has to press a manual button to release the locks on the robotic arm, which then allows the surgeon to manually move the arm into the desired position. Because of the numerous segments on a typical robotic arm, it is sometimes difficult to move the arm such that the whole arm (i.e., all the segments) are correctly positioned. In addition, the conventional setup requires the surgeon to touch the robotic device to position it, which can create risks for contamination during surgery.

Therefore, it would be desirable to have an improved system for manually moving a robotic arm during a medical procedure.

SUMMARY

One aspect of the present disclosure provides an automated positioning device for use in a medical procedure. The automated positioning device comprises a computing device having a processor coupled to a memory, a multi-joint positioning arm electrically coupled to the computing device and controlled by the computing device, and a sensor module attached to the multi-joint positioning arm and providing a proximity signal to the computing device indicating proximity of a target. The computing device provides a control signal to the multi-joint positioning arm to move the multi-joint positioning arm in response to the proximity signal.

The target may include a sensor tag. The computing device may detect presence of the target within a threshold distance of the sensor module and move the multi-joint positioning arm to follow the target. Following the target may include avoiding the target by not contacting the target. The multi-joint positioning arm may include a number of linear arm segments connected by joints with the sensor module attached to a joint of the multi-joint positioning arm. The computing device may detect presence of the target within a threshold distance of the sensor module and move the multi-joint positioning arm to follow the target. The automated positioning device may include a plurality of sensor modules, where each of the plurality of sensor modules is attached to a different joint of the multi-joint positioning arm.

Another aspect of the present disclosure provides a method of controlling a multi-joint positioning arm for use in a medical procedure. The multi-joint positioning arm is electrically coupled to a computing device and controlled by the computing device. The multi-joint positioning arm has a sensor module attached to the multi-joint positioning arm and provides a proximity signal to the computing device indicating proximity of a target. The method comprises receiving the proximity signal and providing a control signal to the multi-joint positioning arm to move the multi-joint positioning arm in response to the proximity signal.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
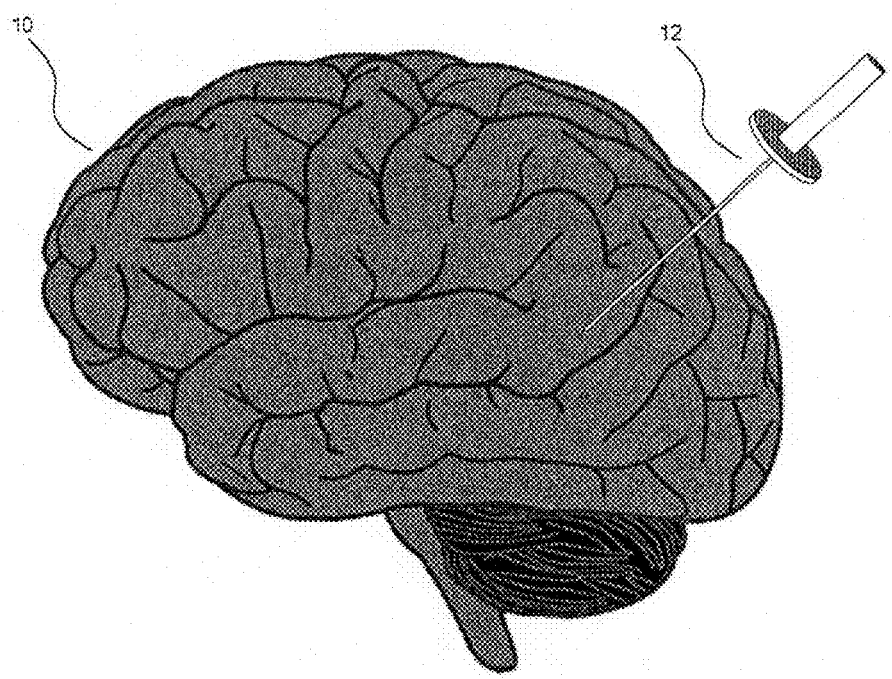
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, wellknown or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12.

Figure 2:
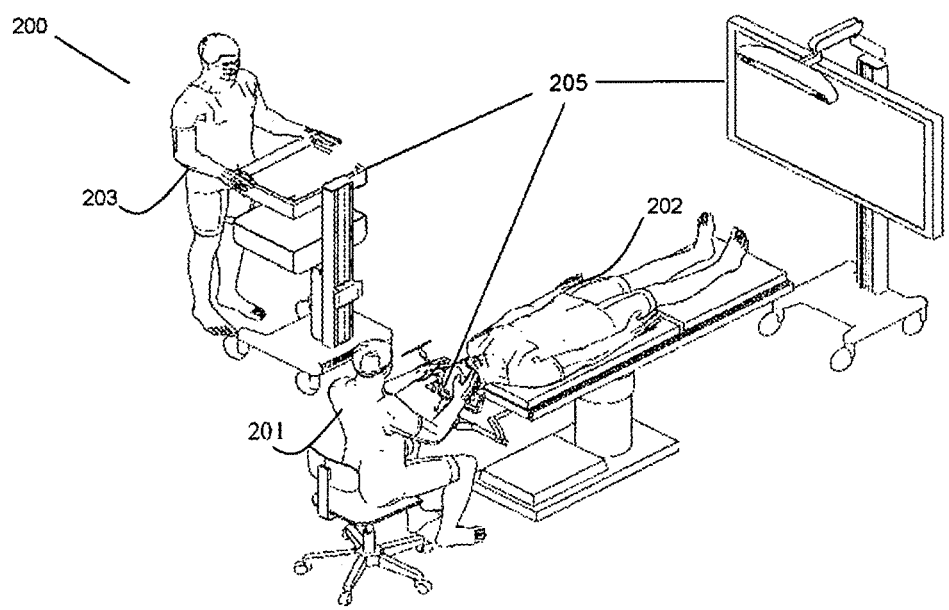
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
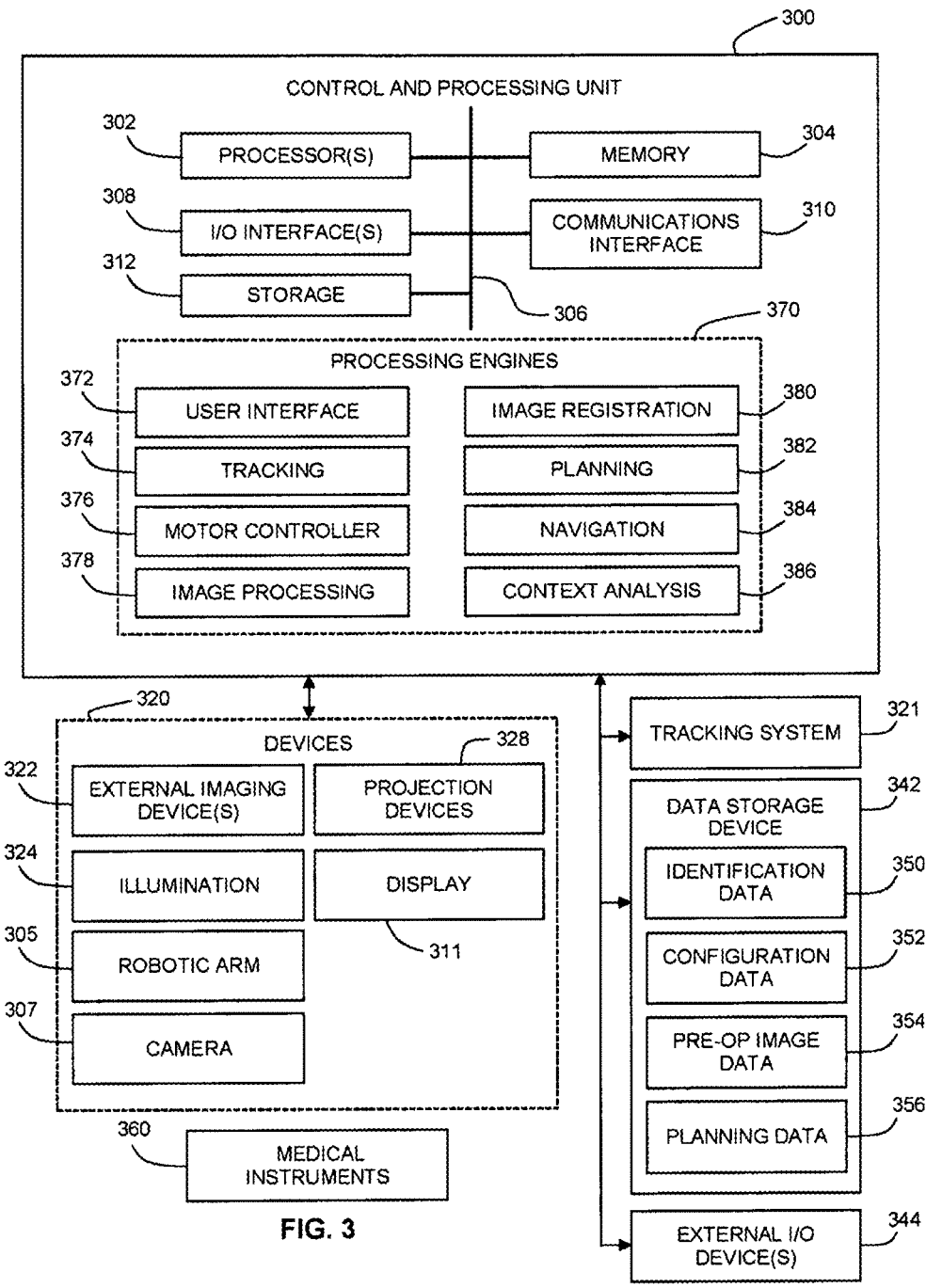
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 205 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a positioning device arm 305, one or more projection devices 328, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
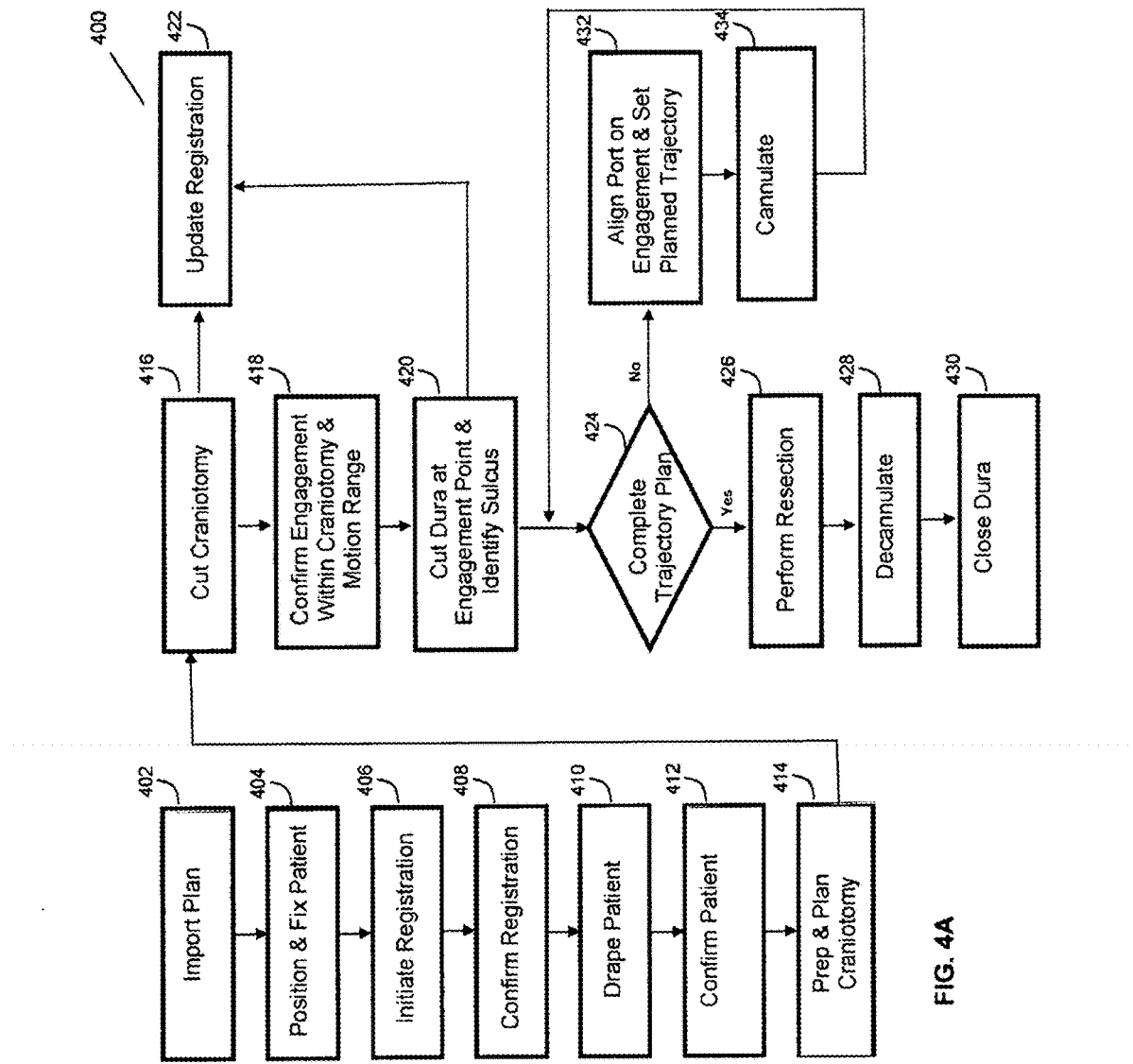
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
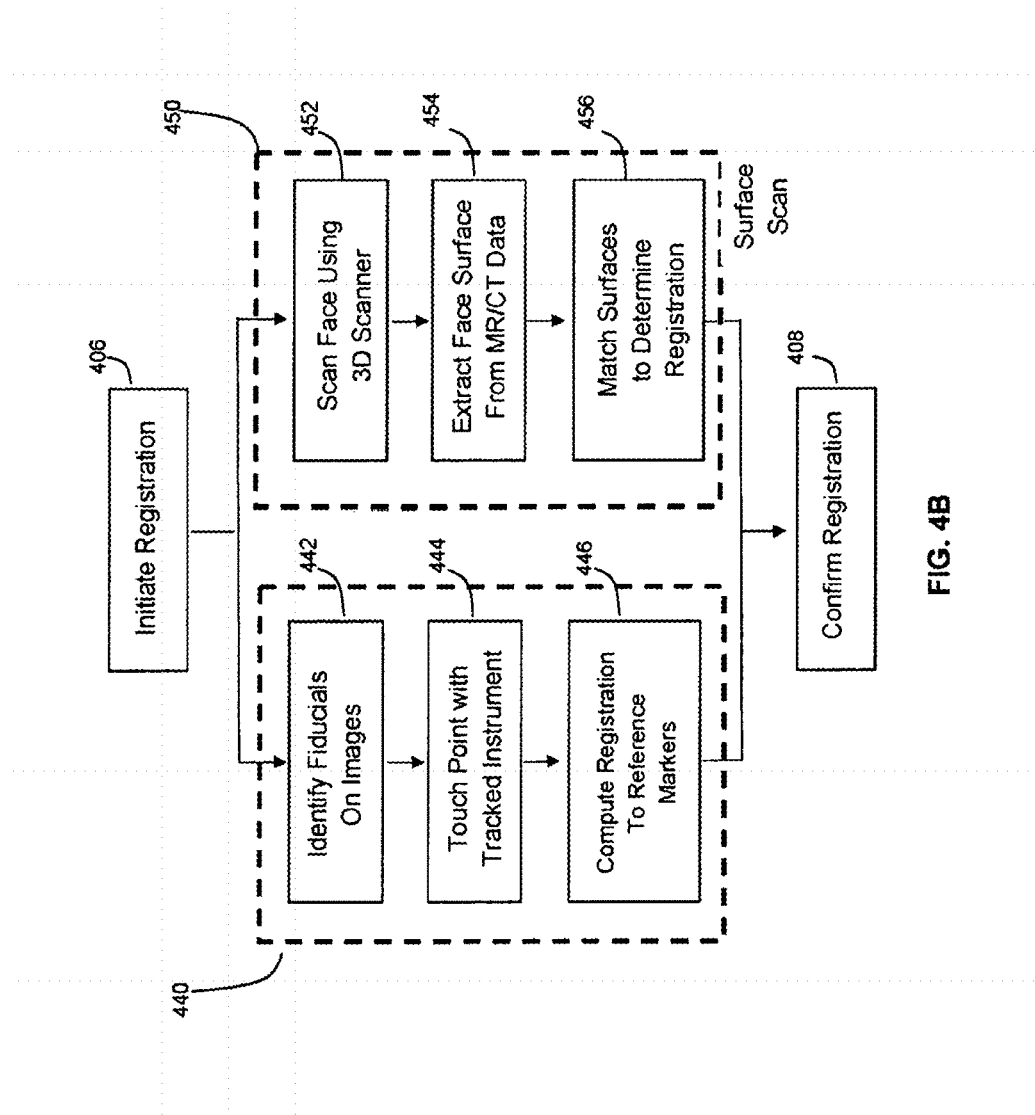
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
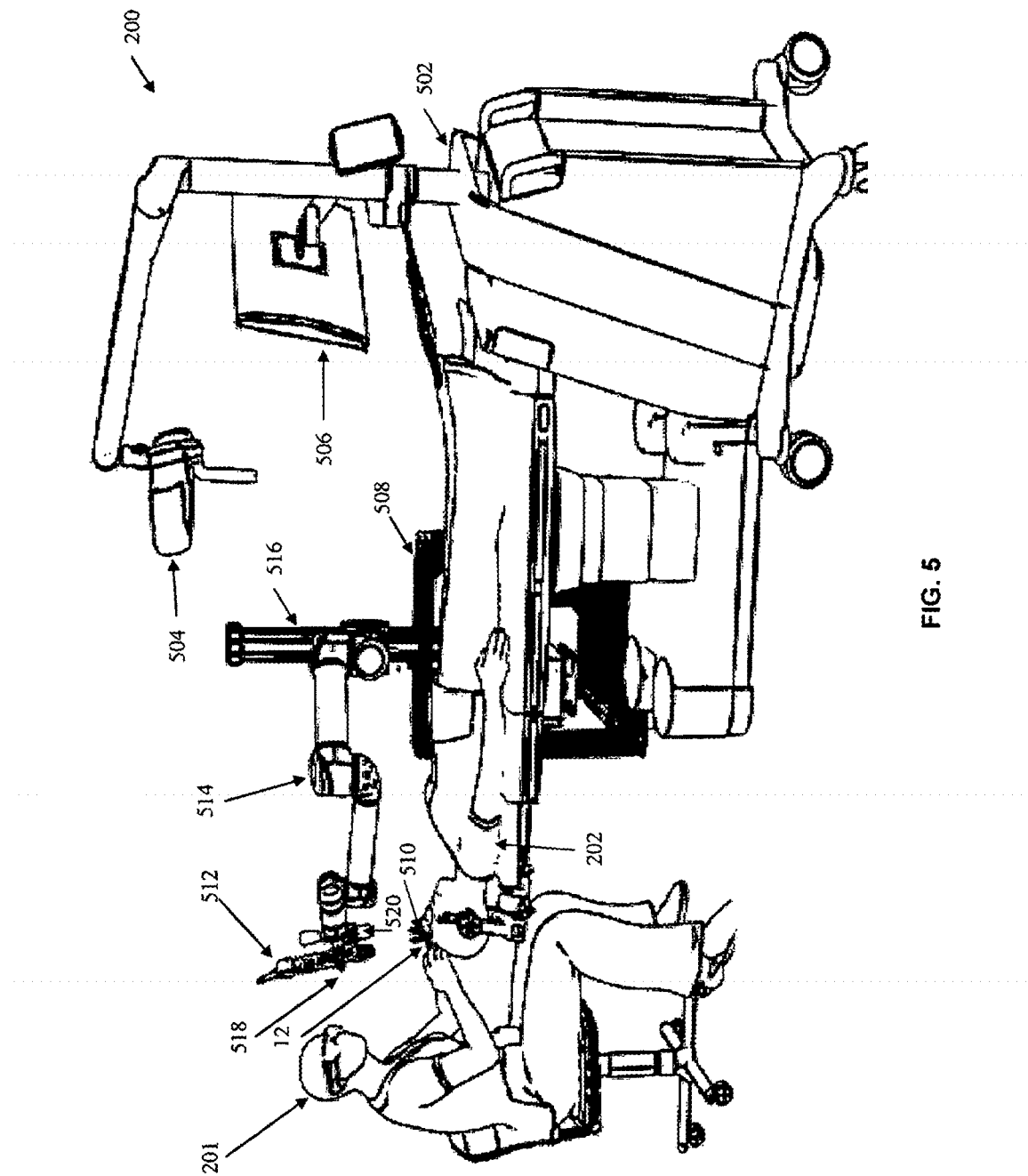
FIG. 5 is a diagram illustrating components of an exemplary surgical system similar to FIG. 2 and also having an automated positioning device used in surgery.

FIG. 5 is a diagram illustrating components of an exemplary surgical system used in port based surgery that is similar to FIG. 2. FIG. 5 illustrates a navigation system 200 having an equipment tower 502, tracking system 504, display 506, an intelligent positioning system 508 and tracking markers 510 used to tracked instruments or an access port 12. Tracking system 504 may also be considered an optical tracking device or tracking camera. In FIG. 5, a surgeon 201 is performing a tumor resection through a port 12, using an imaging device 512 to view down the port at a sufficient magnification to enable enhanced visibility of the instruments and tissue. The imaging device 512 may be an external scope, videoscope, wide field camera, or an alternate image capturing device. The imaging sensor view is depicted on the visual display 506 which surgeon 201 uses for navigating the port's distal end through the anatomical region of interest.

An intelligent positioning system 508 comprising an automated arm 514, a lifting column 516 and an end effector 518, is placed in proximity to patient 202. Lifting column 516 is connected to a frame of intelligent positioning system 508. As seen in FIG. 5, the proximal end of automated mechanical arm 514 (also referred to herein as a multi-joint positioning device or arm) is connected to lifting column 516. In other embodiments, automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

End effector 518 is attached to the distal end of automated arm 514. End effector 518 may accommodate a plurality of instruments or tools that may assist surgeon 201 in his procedure. End effector 518 is shown as holding an external scope, however it should be noted that this is merely an example and alternate devices may be used with the end effector 518 such as a wide field camera, microscope and OCT (Optical Coherence Tomography) or other imaging instruments. In another example, multiple end effectors may be attached to the distal end of automated arm 518, and thus assist the surgeon 201 in switching between multiple modalities. For example, the surgeon 201 may want the ability to move between microscope, and OCT with stand-off optics. In a further example, the ability to attach a second, more accurate, but smaller range end effector such as a laser based ablation system with micro-control may be contemplated.

The intelligent positioning system 508 receives as input the spatial position and pose data of the automated arm 514 and target (for example the port 12) as determined by tracking system 504 by detection of the tracking markers on the wide field camera on port 12. Further, it should be noted that the tracking markers may be used to track both the automated arm 514 as well as the end effector 518 either collectively or independently. It should be noted that a wide field camera 520 is shown in this image and that it is connected to the external scope (e.g., imaging device 512) and the two imaging devices together are held by the end effector 518. It should additionally be noted that although these are depicted together for illustration that either imaging device could be utilized independently of the other, for example where an external video scope can be used independently of the wide field camera 520.

Intelligent positioning system 508 computes the desired joint positions for automated arm 514 so as to maneuver the end effector 518 mounted on the automated arm's distal end to a predetermined spatial position and pose relative to the port 12. This redetermined relative spatial position and pose is termed the "Zero Position" where the sensor of imaging device 512 and port 12 are axially aligned.

Further, the intelligent positioning system 508, optical tracking device 504, automated arm 514, and tracking markers 510 form a feedback loop. This feedback loop works to keep the distal end of the port 12 (located inside the brain) in constant view and focus of the end effector 518 given that it is an imaging device as the port position may be dynamically manipulated by the surgeon during the procedure. Intelligent positioning system 508 may also include a foot pedal for use by the surgeon 201 to align the end effector 518 (i.e., holding a videoscope) of automated arm 514 with the port 12.

Figure 6:
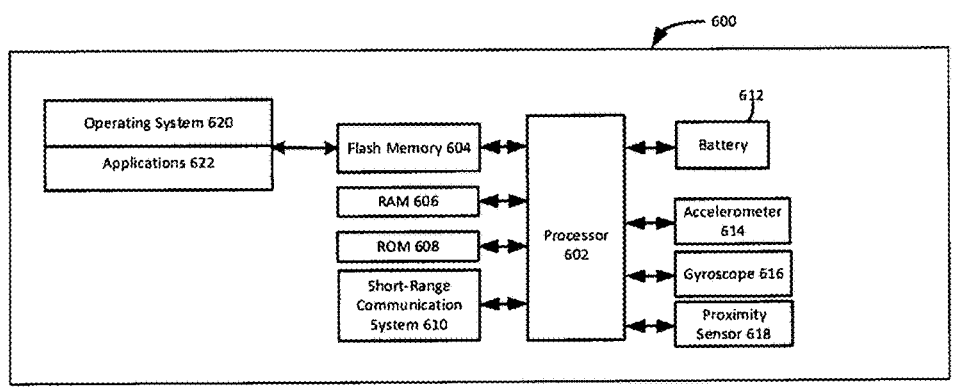
FIG. 6 is a block diagram showing an exemplary sensor module for use with a positioning device of a navigation system.

Referring now to FIG. 6, a block diagram is shown illustrating an exemplary sensor module 600 for use with a multi-joint positioning device, such as automated mechanical arm 514. The sensor module 600 may used be for attachment to the automated mechanical arm 514 and for use with a medical navigation system, such as the medical navigation system 205 including the control and processing unit or system 300. The sensor module 600 generally includes a housing for housing components of the sensor module and for attaching to the automated mechanical arm 514. The sensor module 600 includes a processor 602 housed in the housing, a memory 604 coupled to the processor 602, a communication component coupled to the processor such as the short-range communication system 610, a battery 612 coupled to the processor, and a sensor 618 coupled to the processor. In one example, the sensor 618 may be a proximity based sensor such as a radio-frequency identification (RFID) sensor, a body heat sensor, an optical sensor, or a motion sensor. While the flash memory 604 is provided as one example of a memory coupled to the processor 602, other or additional forms of memory may be coupled to the processor 602, such as a RAM 606 and a ROM 608. The sensor module 600 may operate under stored program control, for example under the direction of an operating system or firmware 620 and/or one or more applications 622, which may be stored in the flash memory 604. Optionally, the sensor module 600 may include additional sensors such as an accelerometer 614 and/or a gyroscope 616.

The communication component 610 includes a wireless communications component and, for example, may use existing wireless standards such as Bluetooth, Wifi, or Zigbee, or may use a suitable yet to be developed wireless standard for communication with a wireless communications subsystem (e.g., the communications interface 310) of the control and processing unit 300 of the medical navigation system 205. Alternatively, the sensor module 600 may connect to a computing device with a wired connection. Several of the components of the sensor module 600 may be optional, depending on the design criteria of a particular application, such as the battery 612, the operating system 620, the applications 622, the short-range communications system 610, and/or the ram 606. In one example, the sensor module 600 may be as simple as the proximity sensor 618 directly coupled to a computing device by a physical wire.

Figure 7:
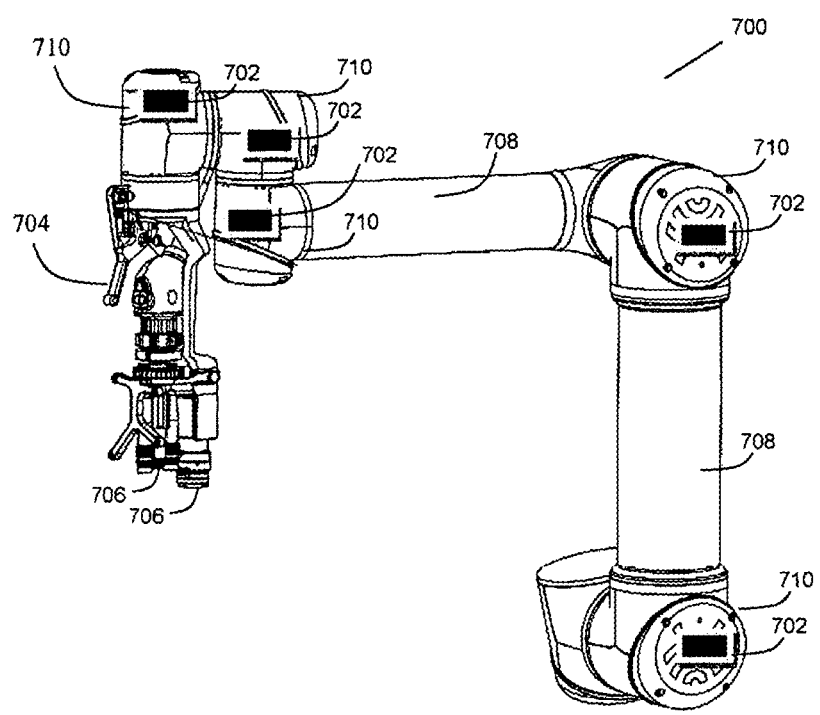
FIG. 7 is perspective drawing illustrating an automated positioning device having an sensor module.

Referring to FIG. 7, a perspective drawing is shown illustrating a multi-joint positioning arm 700 having a sensor module 702 attached thereto in accordance with one aspect of the present disclosure. The multi-joint positioning arm 700 may be part of a larger automated positioning device for use in a medical procedure. The automated positioning device may include a controller. In one example, the function of the controller may be performed by a computing device such as control and processing unit 300 (FIG. 3) having the processor 302 coupled to the memory 304. The automated positioning device further includes the multi-joint positioning arm 700 that is electrically coupled to the computing device 300 and is controlled by the computing device 300. The automated positioning device further has the sensor module 702 attached to the multi-joint positioning arm 700 and providing a proximity signal to the computing device 300 indicating proximity of a target. In one example, the multi-joint positioning arm 700 also includes an end effector 704 that holds one or more imaging devices 706.

In one example, the computing device 300 provides a control signal to the multi-joint positioning arm 700 to move the multi-joint positioning arm 700 in response to the proximity signal. In one example, the target detected by the sensor module 702 may include a sensor tag (not shown). The sensor tag may include an arm band wearable by a surgeon performing a medical procedure, where the sensor tag is integrated into the arm band. In another example, the sensor tag may include a surgical glove wearable by a surgeon performing a medical procedure, where the sensor tag is integrated into the surgical glove. While some examples of suitable attachment mechanisms are provided for attaching the sensor tag to the hand or arm of a surgeon, any suitable attachment mechanism may be used to meet the design criteria of a particular application.

The computing device 300 may detect presence of the target (e.g., the sensor tag) within a threshold distance of the sensor module 702 and the computing device 300 may then move the multi-joint positioning arm 700 to follow the target. In one example, a surgeon may have a sensor tag integrated into a surgical glove that is being worn on a hand. The multi-joint positioning arm 700 may be automatically positioning the end effector 704 such that imaging devices 706 are automatically being pointed at and focusing on a surgical site of interest that is being shown on a display that the surgeon is referencing while performing a medical procedure. When the surgeon decides that the position of the multi-joint positioning arm 700 is not ideal because the arm 700 is interfering with the surgeon, the surgeon may move the hand wearing the surgical glove near to the sensor module 702 on the portion of the multi-joint positioning arm 700 that is interfering with the surgeon. The surgeon's hand is detected by the sensor module 702 when the sensor tag on the hand approaches the sensor module 702 within a threshold distance, such as within 2 cm. Thereafter, the multi-joint positioning arm 700 may move such that the portion of the multi-joint positioning arm 700 attached to the sensor module 702 that detected the surgeon's hand follows the surgeon's hand as if the surgeon has just grabbed the portion of the arm 702 that is in his way and physically pushed, pulled, or otherwise moved it out of the way. The multi-joint positioning arm 700 may adjust itself (e.g., under control of the computing device 300) such that the portion of the multi-joint positioning arm 700 attached to the sensor module 702 that detected the surgeon's hand moves along with the surgeon's hand (e.g., the portion may follow the surgeon's hand at a distance close to the threshold distance) and therefore out of the surgeon's way while maintaining the position of the end effector 704 such that imaging devices 706 may remain focused on the surgical site of interest.

The multi-joint positioning arm 700 includes a number of linear arm segments 708 connected by joints 710. The sensor module 702 may be attached to a joint 710 of the multi-joint positioning arm 700 and the computing device 300 may detect presence of the target within a threshold distance of the sensor module and move the multi-joint positioning arm 700 to follow the target, as described above. The automated positioning device may further include a plurality of sensor modules 702 such as five sensor modules shown as an example in FIG. 7. Each of the plurality of sensor modules 702 may be attached to a different joint 710 of the multi-joint positioning arm 700.

While an example of a 2 cm threshold distance is provided, any suitable threshold distance (e.g., 1 cm, 5 cm, 10 cm) may be used to meet the design criteria of a particular application. Further, while five sensor modules 702 are shown in FIG. 7, any suitable number of sensor modules 702 may be used to meet the design criteria of a particular application.

Alternatively, the sensor modules 702 may be attached to the linear arm segments 708 of the multi-joint positioning arm 700. In one example, the sensor modules 702 may be attached approximately to the centers of the linear arm segments 708. The computing device 300 may be configured to detect presence of the target within the threshold distance of the sensor module 702 and move the multi-joint positioning arm 700 to follow the target, as described above. The automated positioning device may include a plurality of sensor modules where each of the plurality of sensor modules is attached to a different linear arm segment of the multi-joint positioning arm 700.

In one example, the sensor module (e.g., sensor module 702, 600) may include a housing for housing components of the sensor module and for attaching to the multi-joint positioning arm 700. The sensor module may include a processor housed in the housing, a memory coupled to the processor, a wireless communication component coupled to the processor for communicating with a wireless communication component of the computing device 300, a battery coupled to the processor, and a sensor coupled to the processor. Alternatively the sensor module may be connected to the computing device 300 with a wired connection.

In one example, the sensor module 702 may be a radio-frequency identification (RFID) sensor and the target may be an RFID sensor tag. In another example, the sensor module 702 may be a body heat sensor and the target may be human skin that emits an elevated temperature relative to the ambient air temperature. In another example, the sensor module 702 may be an optical sensor and the target may be, for example, an optical tracking marker. In yet another example, the sensor module 702 may be a motion sensor and the computing device 300 may be configured to detect motion of a hand or other body part approaching the motion sensor within a threshold distance.

The computing device 300 may provide the control signal to move joints of the multi-joint positioning arm 700 such that when the target approaches the sensor module 702 within the threshold distance and continues to move, the joint 710 attached to the sensor module 702 follows the target, as described above. In yet another example, the computing device 300 provides the control signal to move joints 710 of the multi-joint positioning arm 700 such that when the two targets (e.g., two hands each wearing a sensor tag attached to a surgical glove) approach two of the plurality of sensor modules 702 within the threshold distance and continue to move, the joints attached to the two of the plurality of sensor modules 702 follow the targets. In other words, the surgeon may use both hands to move two joints 710 or linear segments 708 that are interfering with him out of the way by bringing his hands close to the joints 710 or linear segments 708, at which point the computing device 300 controls the multi-joint positioning arm 700 such that the joints 710 or linear segments 708 that are attached to the sensor modules that detected the tags will follow the surgeon's hands as the hands continue to move.

Figure 8:
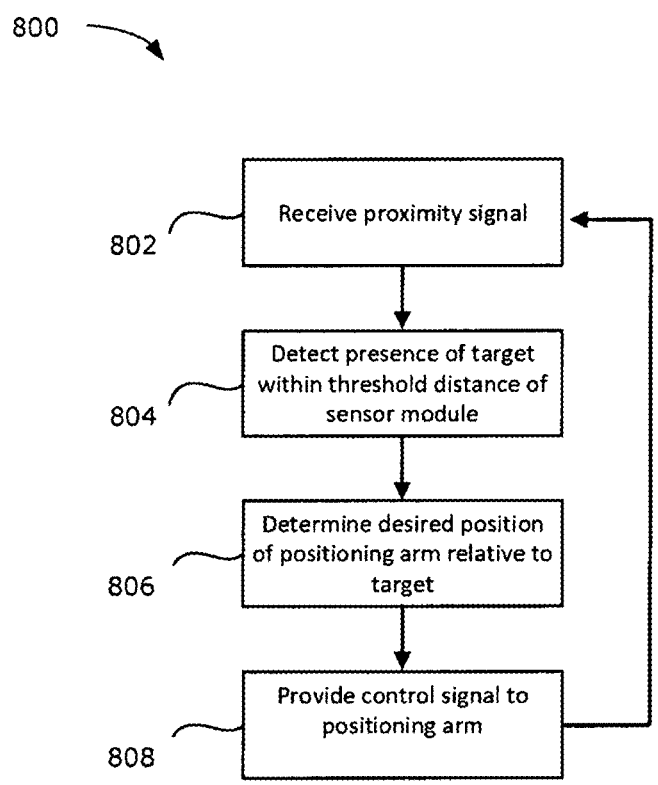
FIG. 8 is a block diagram showing in flow chart form a method for controlling a multi-joint positioning arm.

Referring to FIG. 8, a block diagram is shown illustrating in flow chart form a method 800 for controlling a multi-joint positioning arm. The method of controlling the multi-joint positioning arm (e.g., the multi-joint positioning arm 700) may be for use in a medical procedure and the multi-joint positioning arm may be electrically coupled to a computing device (e.g., control and processing unit 300) and controlled by the computing device. The multi-joint positioning arm has a sensor module (e.g., the module 702) attached to the multi-joint positioning arm and providing a proximity signal to the computing device indicating proximity of a target.

At a first block 802, the computing device receives the proximity signal from one or more sensor modules, such as the sensor modules 702 shown in FIG. 7.

Next, at a block 804, the computing device detects the presence of the target within a threshold distance of the sensor module based on the received proximity signal. For example, the surgeon may be wearing a surgical glove having an RFID sensor embedded therein and the computing device may determine that the threshold has been crossed when the proximity signal indicates that the RFID sensor has approached one of the sensor modules within a distance of 2 cm or less. While 2 cm is used as an exemplary threshold distance for activating a sensor tag following mode of the multi-joint positioning arm, any suitable threshold distance may be used to meet the design criteria of a particular application, such as 1 cm, 2 cm, 5 cm, 10 cm, etc.

Next at a block 806, the computing device determines the desired position of the multi-joint positioning arm relative to the target. For example, the method 800 may represent an iterative process that is repeatedly executed by the computing device and the distance of a sensor tag relative to the sensor module is continually monitored. Once the computing device determines that a sensor tag has approached the sensor module within the threshold distance and the sensor tag then continues to move relative to the sensor module, the computing device may determine adjustments to be made to the joints of the multi-joint positioning arm such that the joint or linear segment (e.g., 710, 708) to which the sensor module is attached where the threshold has been satisfied will follow the sensor tag as it moves and the other joints of the multi-joint positioning arm will adjust in a way that allows the sensor module to follow the sensor tag yet still retain the focus of the multi-joint positioning arm. In other words and in one example, if one of the cameras 706 is focused on a surgical site of interest, the multi-joint positioning arm will be moved in such a way that one of the cameras 706 remains focused on the surgical site of interest while the sensor module follows the sensor tag.

Once the desired position of the multi-joint positioning arm is determined at the block 806, the needed control signal is provided by the computing device to the multi-joint positioning arm such that the multi-joint positioning arm will assume the desired position at a block 808. The control signal is provided to the multi-joint positioning arm to move the multi-joint positioning arm to follow the target in response to the proximity signal.

As discussed above, the sensor module used by the method 800 may be a radio-frequency identification (RFID) sensor and the target may be an RFID sensor tag. In another example, the sensor module may be a body heat sensor and the target may be human skin that emits an elevated temperature relative to the ambient air temperature. In another example, the sensor module may be an optical sensor and the target may be, for example, an optical tracking marker that may be worn on the arms of the surgeon. In yet another example, the sensor module may be a motion sensor and the computing device may be configured to detect motion of a hand or other body part approaching the motion sensor within a threshold distance. The method 800 may be applicable to any of these sensor/target configurations, or any other suitable type of sensor/target configuration.

In another example, block 808 may operate such that providing the control signal to the multi-joint positioning arm to move the multi-joint positioning arm to follow the target includes moving joints of the multi-joint positioning arm such that when the target approaches the sensor module within the threshold distance and continues to move the joint attached to the sensor module follows the target. In yet another example, block 808 may operate such that providing the control signal to the multi-joint positioning arm to move the multi-joint positioning arm to follow the target includes moving joints of the multi-joint positioning arm such that when the two targets approach two of the plurality of sensor modules within the threshold distance and continue to move the joints attached to the two of the plurality of sensor modules follow the targets.

Further, the multi-joint positioning arm 700 and the method 800 may operate with an additional input device, such as a foot pedal connected to the processing device 300, such as for safety reasons. In one example, the multi-joint positioning arm 700 may not move unless the foot pedal is depressed. If a surgeon wishes to make use of the method 800, the surgeon may depress the foot pedal first, execute the method 800, and stop the target following mode of the multi-joint positioning arm 700 simply by removing his foot from the foot pedal.

In another example, if the surgeon moves his hand up to a joint 710 and engages the joint 710 (e.g., as described at block 804), then the surgeon can move his hand and the joint 710 will follow. In another example, the surgeon may rotate his hand around the joint, which may be detected by one or more of the sensor modules 702, which may result in the joint 710 rotating. In other words, the sensor modules 702 may be used by the computing device to enact either a translation of the joint or to enact a rotation of the joint, or both, depending on the design criteria of a particular application. In the case where input from the sensor modules 702 is used to enact a rotation of the joint 710, multiple sensor modules 702 may be placed around the joint 710.

One aspect of the present description provides that each joint 710 of the multi-joint positioning arm 700 detects when a surgeon's hand (e.g., the target) is held nearby. When the hand is detected at a joint 710, the processing device 300 calculates the optimal way to move all higher joints 710 (e.g., joints 710 higher up the multi-joint positioning arm 700, away from the end effector 704) such that the joint 710 moves to where the hand is located. Once the joint 710 is engaged with the target, the doctor can then start moving his hand to guide the multi-joint positioning arm 700 further. As such, the doctor than can just use his hands without physically touching the multi-joint positioning arm 700 to reposition the multi-joint positioning arm 700.

Many methods may be used to detect the hand near the joint 710. One simple implementation may be to have an RFID on the surgeon's hand (e.g., as a wristband) and an RFID detector on each joint 710. The movement action is triggered at a joint 710 when the sensor 702 on the joint 710 detects the surgeon's hand. Further, both hands may be used at two different joints 710 to define a specific orientation of a linear arm segment 708 for the multi-joint positioning arm 700. Instead of manipulating one joint 710 at a time to configure a more complex movement of the multi-joint positioning arm 700, it may be possible to use two hands to define more specific positions/movements.

The computing device 300 may further have additional features that are configurable when operating the method 800, such as getting the multi-joint positioning arm 700 to an initial ready position, using a pointer to define a "no go" area in space where the multi-joint positioning arm 700 is not permitted to breach, providing different following modes such as a close following mode or a natural action mode, a freeze joint mode, a hybrid envelope mode, and a gesture mode. In another example, the sensor module 600 may be a wearable sensor similar to that offered by Thalmic Labs. In alternate embodiments, sensor module 600 may also be integrated into other wearable technologies such as the FitBit, Fuelband, smart watches and/or wearable clothing and gloves worn by the surgical team. In another example, the method 800 may be used to preposition the multi-joint positioning arm 700 prior to surgery.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. An automated positioning device for use in a medical procedure, the automated positioning device comprising:
   a computing device having a processor coupled to a memory;
   a multi-joint positioning arm having a number of linear arm segments connected by joints, the multi-joint positioning arm being electrically coupled to the computing device and controlled by the computing device; and a plurality of sensor modules each attached to at least one of a different joint and linear arm segment of the multi-joint positioning arm and each providing a proximity signal to the computing device indicating proximity of a respective one of a plurality of targets, wherein the computing device provides a control signal to the multi-joint positioning arm to move the multi-joint positioning arm in response to the proximity signals and the computing device detects presence of the targets within a threshold distance of the sensor modules and moves the multi-joint positioning arm to follow the targets, wherein the computing device provides the control signal to move the joints of the multi-joint positioning arm such that when two of the targets approach two of the plurality of sensor modules within the threshold distance and continue to move, the joints or linear arm segments attached to the two of the plurality of sensor modules follow the targets, wherein the targets includes at least one sensor tag.

2. The automated positioning device according to claim 1, wherein following the targets includes avoiding the targets by not contacting the targets.

3. The automated positioning device according to claim 1, wherein the sensor module includes:
   a housing for housing components of the sensor module and for attaching to the multi-joint positioning arm;
   a processor housed in the housing;
   a memory coupled to the processor;
   a wireless communication component coupled to the processor for communicating with a wireless communication component of the computing device;
   a battery coupled to the processor; and
   a sensor coupled to the processor.

4. The automated positioning device according to claim 1, wherein the sensor module includes:
   a housing for housing components of the sensor module and for attaching to the multi-joint positioning arm;
   a processor housed in the housing;
   a memory coupled to the processor; and
   a sensor coupled to the processor,
   wherein the sensor module is connected to the computing device with a wired connection.

5. The automated positioning device according to claim 1, wherein the at least one sensor tag includes an arm band wearable by a surgeon performing a medical procedure.

6. The automated positioning device according to claim 1, wherein the at least one sensor tag includes a surgical glove wearable by a surgeon performing a medical procedure.

7. The automated positioning device according to claim 1, wherein the sensor module is selected from the group consisting of a radio-frequency identification (RFID) sensor, a body heat sensor, an optical sensor, an accelerometer, a gyroscope and a motion sensor.

8. A method of controlling a multi-joint positioning arm for use in a medical procedure, the multi-joint positioning arm having a number of linear arm segments connected by joints, the multi-joint positioning arm being electrically coupled to a computing device and controlled by the computing device, the multi-joint positioning arm having a plurality of sensor modules each attached to at least one of a different joint and linear arm segment of the multi-joint positioning arm and each providing a proximity signal to the computing device indicating proximity of a respective one of a plurality of targets, the method comprising:
   receiving the proximity signals;
   detecting presence of the targets within a threshold distance of the sensor modules based on the received proximity signals; and
   providing a control signal to the multi-joint positioning arm to move the multi-joint positioning arm to follow the targets in response to the proximity signals by moving the joints of the multi-joint positioning arm such that when two targets approach two of the plurality of sensor modules within the threshold distance, continuing to move the joints and linear arm segments attached to the two of the plurality of sensor modules to follow the targets, wherein the target includes at least one sensor tag.

9. The method according to claim 8, wherein the at least one sensor tag includes an arm band wearable by a surgeon performing a medical procedure.

10. The method according to claim 8, wherein the at least one sensor tag includes a surgical glove wearable by a surgeon performing a medical procedure.

11. The method according to claim 8, wherein the sensor module is selected from the group consisting of a radio-frequency identification (RFID) sensor, a body heat sensor, an optical sensor, and a motion sensor.

12. The method according to claim 8, wherein following the targets includes avoiding the targets by not contacting the targets.

* * * * *